United States Patent
Guo et al.

(10) Patent No.: US 6,632,200 B2
(45) Date of Patent: Oct. 14, 2003

(54) HEMOSTASIS VALVE

(75) Inventors: Xiaoping Guo, Bloomington, MN (US); Richard Stehr, Stillwater, MN (US); Daniel J. Potter, Stillwater, MN (US)

(73) Assignee: St. Jude Medical, Daig Division, Minnetonka, MN (US)

( * ) Notice: Subject to any disclaimer, the term of this patent is extended or adjusted under 35 U.S.C. 154(b) by 289 days.

(21) Appl. No.: 09/734,391

(22) Filed: Dec. 11, 2000

(65) Prior Publication Data

US 2002/0010425 A1 Jan. 24, 2002

Related U.S. Application Data

(63) Continuation-in-part of application No. 09/491,221, filed on Jan. 25, 2000.

(51) Int. Cl.$^7$ .............................................. A61M 5/00
(52) U.S. Cl. ................. 604/247; 604/167.04; 604/256
(58) Field of Search ........................ 604/245, 247, 604/167.01, 167.02, 167.03, 167.04, 167.06; 251/149.1, 149.2

(56) References Cited

U.S. PATENT DOCUMENTS

| | | | |
|---|---|---|---|
| 2,023,267 A | 12/1935 | De Saint-Rapt et al. | |
| 4,000,739 A | 1/1977 | Stevens | |
| 4,430,081 A | 2/1984 | Timmermans | |
| 4,436,519 A | 3/1984 | O'Neill | |
| 4,610,655 A | 9/1986 | Muller | |
| 4,615,531 A | 10/1986 | Green | |
| 4,626,245 A | 12/1986 | Weinstein | |
| 4,629,450 A | 12/1986 | Suzuki et al. | |
| 4,655,752 A | 4/1987 | Honkanen et al. | |
| 4,673,393 A | 6/1987 | Suzuki et al. | |
| 4,705,511 A | 11/1987 | Kocak | |
| 4,723,550 A | 2/1988 | Bales et al. | |
| 4,798,594 A | 1/1989 | Hillstead | |
| 4,895,346 A | 1/1990 | Steigerwald | |
| 4,895,565 A | 1/1990 | Hillstead | |
| 4,909,798 A | 3/1990 | Fleischhacker et al. | |
| 4,917,668 A | 4/1990 | Haindl | |
| 4,960,412 A | 10/1990 | Fink | |
| 5,000,745 A | 3/1991 | Guest et al. | |
| 5,041,095 A | 8/1991 | Littrell | |
| 5,114,408 A | 5/1992 | Fleischhaker et al. | |
| 5,125,903 A | 6/1992 | McLaughlin et al. | |
| 5,149,327 A | 9/1992 | Oshiyama | |
| 5,167,637 A | 12/1992 | Okada et al. | |
| 5,176,652 A | 1/1993 | Littrell | |
| 5,207,656 A | 5/1993 | Kranys | |
| 5,269,764 A | 12/1993 | Vetter et al. | |
| 5,395,349 A | 3/1995 | Quiachon et al. | |
| 5,520,655 A | 5/1996 | Davila et al. | |
| 5,643,227 A | 7/1997 | Stevens | |
| 5,779,697 A | * 7/1998 | Glowa et al. ................ 606/185 |
| 5,858,007 A | 1/1999 | Fagan et al. | |
| 6,024,729 A | * 2/2000 | Dehdashtian et al. ....... 604/256 |

FOREIGN PATENT DOCUMENTS

| | | |
|---|---|---|
| DE | 297 01 600 | 7/1997 |
| EP | 0567142 | 10/1993 |
| WO | WO 98/13083 | 4/1998 |

OTHER PUBLICATIONS

"Linear Atrial Ablation with a Diode Laser and Fiberoptic Catheter," Keane, et al., from *Images in Cardiovascular Medicine*, (1999).

"Slow Intramural Heating with Diffused Laser Light," Ware, et al., (1999).

* cited by examiner

*Primary Examiner*—Brian L. Casler
*Assistant Examiner*—Kevin C. Sirmons
(74) *Attorney, Agent, or Firm*—Scott R. Cox

(57) ABSTRACT

A hemostasis cannula unit including a valve housing, a cap, and a hemostasis valve, wherein the hemostasis valve includes a proximal valve gasket and a distal valve gasket compressed against the valve gasket by the valve housing, wherein the proximal valve gasket is the same shape as the distal valve gasket.

24 Claims, 8 Drawing Sheets

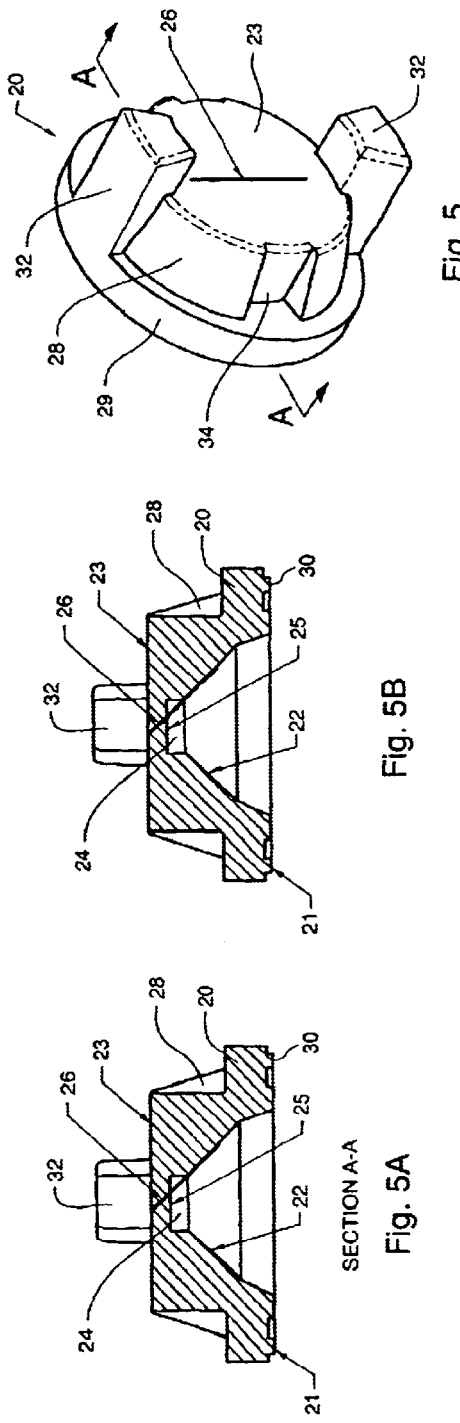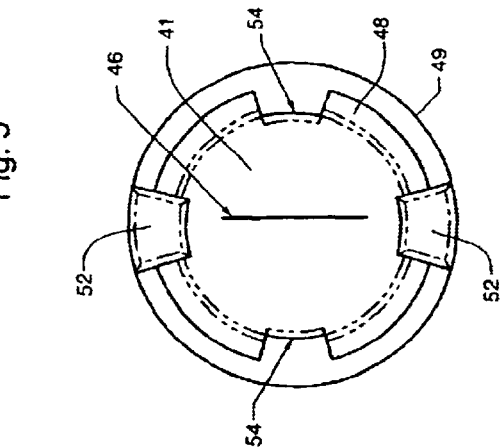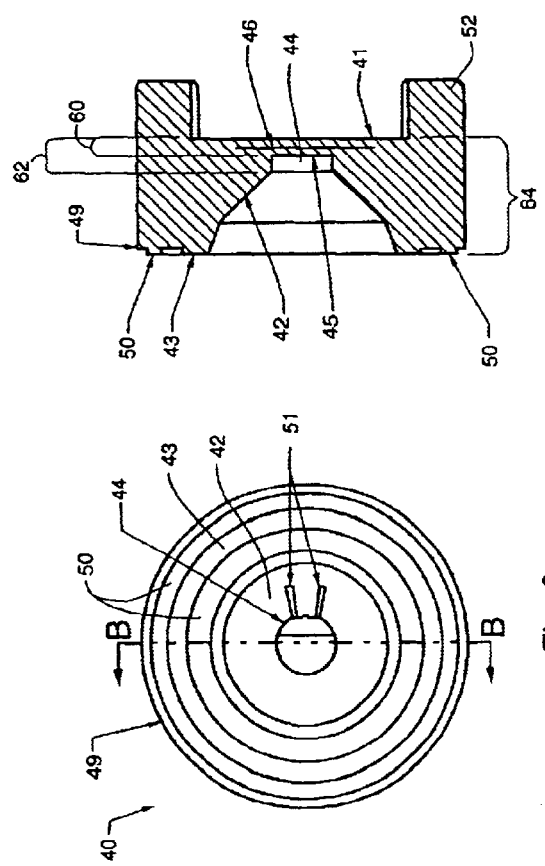

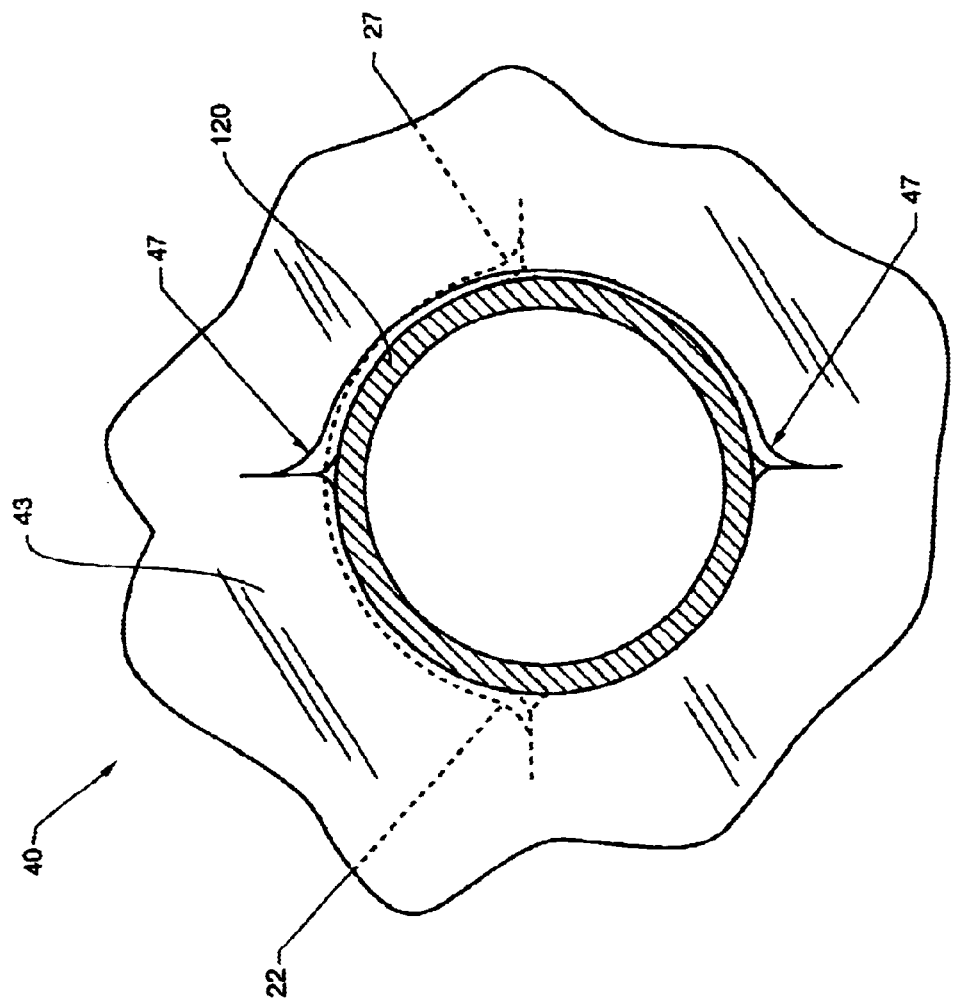

HEMOSTASIS VALVE

CROSS-REFERENCE TO RELATED APPLICATIONS

This application is a continuation-in-part application of application Ser. No. 09/491,221 filed Jan. 25, 2000.

BACKGROUND OF INVENTION

1. Field of Invention

This invention relates to medical devices and instruments. More particularly, this invention relates to hemostasis valves and hemostasis cannula units containing a hemostasis valve, wherein the hemostasis valve is comprised of two separate valve gaskets, each with the same shape, which are reversed in position, but joined together within the valve housing of the hemostasis cannula.

2. Prior Art

The introduction of catheters into blood vessels for a variety of purposes such as coronary angiography has been known for many years. Several techniques for introducing these catheters into the vasculature of the human body are available. One such technique is the cut-down method, while another is the Seldinger technique. The Seldinger technique includes surgically opening a vein or artery with a needle, inserting a guidewire into the vessel through the lumen of the needle, withdrawing the needle, inserting over the guidewire a dilator which has passed through an associated sheath containing a hemostasis valve, removing the dilator and inserting a catheter through the hemostasis valve and sheath into the blood vessel.

A wide variety of hemostasis valves are known in the prior art. However, when a guidewire is inserted through most hemostasis valves, because most guidewires are so small relative to the catheters which may also be employed, it is often difficult for the valve to seal adequately against the backward pressure of blood, while at the same time permitting easy insertion of much larger diameter catheters into the vasculature. This problem is particularly acute with catheterization procedures involving arterial introduction where there is a high reverse pressure of blood. In these arterial procedures, blood can squirt out when the guidewire is introduced through the hemostasis valve. Excessive blood leakage may be extremely dangerous to patients and a contaminant to the operating room and medical personnel. Accordingly, most prior art hemostasis valves are designed for use with only one size of catheter. It has often been difficult to employ a single type of hemostasis valve with catheters of widely varying diameters because adequate sealing around the catheter walls cannot be achieved by these hemostasis valves.

Cardiac catheter introducers used during coronary procedures often contain a hemostasis valve that is mounted in the valve housing or hub, which is secured on the proximal end of the introducer. Such an introducer is conventionally used to facilitate the insertion of catheters and guidewires into the vascular system of a patient, while minimizing injury to the patient at the access site and improving the patient's comfort during the cardiac catheterization procedure. An introducer is particularly necessary where one or more treating catheters of varying diameters are inserted into and removed from the patient's vessel repeatedly as often occurs during angiographic procedures and angioplasty. The mere presence of the catheter introducer and the insertion of different size catheters through the introducer often causes bleeding during cardiac catheterization procedures. A high performance hemostasis valve is therefore needed to seal against the leakage of blood out of or around catheters and guidewires having varying diameters as they enter an artery or other blood vessel. The hemostasis valve must also prevent the introduction of air into the artery or blood vessel of the patient when one or more than one of the elongated catheters or guidewires are withdrawn from the introducer. In addition, the valve must remain sealed when there is no medical device passing through the valve. Accordingly, the requirements for a useful hemostasis valve include at least the following: (a) the valve is always sealed when no elongated cylindrical medical device is introduced through it; (b) the insertion and retraction forces must be minimal when larger diameter catheters (such as those larger than about 9 F (3 mm)) are introduced into the valve; (3) in contrast, the valve must maintain good sealability when small diameter guidewires (such as those down to 0.014 in. (0.35 mm)) pass through its passageway; and (4) to the greatest extent possible, the deformation of the valve should be in a radial direction instead of an axial direction to prevent the transmission of air into the blood stream.

Numerous hemostasis valves are known which can be classified in three major groups. Type I, as disclosed, for example, in U.S. Pat. Nos. 5,041,095 and 5,176,652, contain a pair of disc-like gaskets of approximately equal thickness. Each gasket has a Y-shaped opening cut into the gasket radially extending from its center forming three (3) slits, each located at an angle of about 120 degrees from the other slits. Each slit penetrates the gasket from one end face to the other end face. To form a self-sealing hemostasis valve, the two Y-shaped slits of the respective gaskets are mounted in a position opposite to one another in the valve housing.

Other types of hemostasis valves containing multiple disks which are approximately the same size and thickness are disclosed, for example, in U.S. Pat. Nos. 2,023,267; 4,000,739; 4,430,081; 4,655,752; 4,673,393; 4,895,346; 5,000,745; and 5,643,227. Each of these patents discloses a different combination of valve disks that are used to form the hemostasis valve. In some embodiments, one of the disks contains Y-shaped slits and the other disk contains a circular opening in the center of that disk.

Type II hemostasis valves as disclosed, for example, in U.S. Pat. Nos. 4,626,245; 4,629,450; 5,114,408; 5,149,327 and 5,167,637 and utilize a single sealing disk. This disk generally has a first slit that opens at only one end face and a second slit that opens at only the other end face. The two slits, which form a crisscross, intersect each other inside the disk. Other types of single disk hemostasis valves with different shapes for the opening through that disk are disclosed, for example, in U.S. Pat. No. 4,705,511 (see FIG. 4); U.S. Pat. No. 4,798,594 and 4,895,565.

Type III hemostasis valves, as disclosed, for example, in U.S. Pat. Nos. 5,149,327; 5,207,656 and 5,520,655, are similar to Type II hemostasis valves, but differ in that only one slit (Y-shaped or +-shaped) penetrates from one end face to the other end face of the gasket. The slit may be perpendicular to the body of the valve or it may be spiral cut to form a downwardly spiraling cut, as disclosed in U.S. Pat. Nos. 5,520,655, 4,789,594, and 4,895,565. Note particularly U.S. Pat. No. 4,705,511, which discloses a hemostasis valve with an angled cut extending from its proximal to its distal face.

Other types of hemostasis valves are disclosed in various patents such as in U.S. Pat. Nos. 4,610,655; 4,909,798 and 5,125,903. However, these hemostasis valves are generally designed for use with a particular size of medical device.

Because adequate sealing around the elongated cylindrical medical devices using conventional hemostasis valves cannot be assured for a wide variety of devices, each having a different diameter, it has not been possible to utilize a single hemostasis valve with devices of widely varying diameters. Also, many of the prior art hemostasis valves exhibit various performance defects due to various structural features. For example, it may be difficult to manipulate an elongated cylindrical medical device through the passageway formed by automatically closed slits because no pre-guiding centering channel is provided. In addition, for Type I hemostasis valves, the deformation arising from the insertion of the elongated cylindrical medical device into the valve is generally in an axial direction rather than radially away from the opening. In these hemostasis valves, the introduction of a medical device creates an axial gap between the gaskets that may result in leakage of blood under high blood pressure situations. For Type II hemostasis valves, such axial gaps are sometimes reduced by integrating the sealing function of two gaskets into a single gasket. With this integration the sealability seems to improve in comparison to Type I hemostasis valves. However, the insertion force necessary for insertion of medical devices through the passageway of the valves dramatically increases because the deformation force for the two slits of the hemostasis valve is in opposition to one another and the friction at the intersecting location of the two slits inside the valve increases.

For Type III hemostasis valves, the insertion force may also be a problem. In addition, these valves often do not seal against the leakage of blood when a small-diameter guidewire passes through its slit passageway. Further, the restitutive force created by the retraction of larger-diameter catheters may cause the introduction of air into the blood stream.

It has been recognized that axial deformation of the hemostasis valve should be limited to improve sealability. For example, U.S. Pat. No. 5,520,655 discloses a medical device wherein the valve is pre-deformed in an axial direction opposite to that of the insertion force. The axial deformation induced by the insertion of an elongated medical device is compensated for by this pre-deformation. As a result, the actual deformation during insertion seems to be radial to the valve, thus improving the sealability of the valve. However, the insertion force may increase due to this pre-deformation, and the restitutive force due to the retraction of the elongated cylindrical member may still allow the seepage of air into the blood stream.

U.S. Pat. No. 4,917,668 suggests the use of spring-loaded resilient gasket valve members with one or more spring elements augmenting the natural resilience of the sealing gasket material to improve sealability. However, the insertion force increases with incorporation of metal springs.

In yet another approach to providing a suitable seal under varying conditions encountered in practice, U.S. Pat. No. 5,125,903 discloses the use of concave and convex cusp-shaped surfaces to form the thinned central region of the valve, through which the short intersecting slits extend at a 45 degree angle to the 90 degree line of intersection.

The hemostasis valves described above represent departures from, and attempts to overcome deficiencies in, the flat disk-shaped gaskets involving reduced diameter holes, slits and crossed slits therethrough to accommodate elongated cylindrical medical devices passing through the valve. However, improvements are still necessary to hemostasis valves to overcome problems of the prior art valves.

Accordingly, it is an object of the present invention to prepare a universal hemostasis valve which exhibits high performance in sealing against the leakage of blood, limits the backflow of air into the vessels and eases insertion and retraction of elongated cylindrical medical devices of varying diameters. This hemostasis valve may be reliably used with a wide variety of both large catheters, up to about 9 F (3 mm), and small guidewires, down to 0.014 in. (0.35 mm).

It is a further object of the invention to disclose a hemostasis valve composed of two separate valve gaskets which are formed in the same shape, and which are joined together to form the hemostasis valve.

It is a further object of the invention to disclose a hemostasis valve comprising a proximal valve gasket and a distal valve gasket, wherein each of the valve gaskets contains at least one positioning protrusion and at least one positioning slot which interact with each other to orient the two valve gaskets in a particular position relative to each other.

It is a still further object of the invention to disclose a hemostasis valve comprising a pair of valve gaskets, wherein the center of each valve gasket is very thin in relation to the overall thickness of the valve gasket.

It is a still further object of the invention to disclose a hemostasis valve comprising a pair of valve gaskets, each containing a slit, wherein each of the slits is angled at an angle of from 85 degrees to about 30 degrees to the position of the surface of each valve gasket.

It is a still further object of the invention to disclose a hemostasis valve comprising a pair of valve gaskets, wherein each contains a conical receiving area and a guiding hole to guide medical devices through the hemostasis valve.

It is a still further object of the invention to disclose a hemostasis valve, comprising a pair of valve gaskets, each of which contains a beveled edge which extends toward the valve housing when a medical device is inserted through the hemostasis valve.

It is a still further object of the invention to disclose a hemostasis valve comprising a pair of valve gaskets which maintain substantial contact against each other when a medical device passes through the hemostasis valve.

It is still further object of the invention to disclose a hemostasis valve comprising a pair of identical valve gaskets joined together, wherein the entry face of the proximal valve gasket and the exit face of the distal valve gasket contain axially compressible concentric rings.

It is a still further object of the invention to disclose a hemostasis cannula unit including a valve housing, a cap and a hemostasis valve, wherein the hemostasis valve comprises a pair of identical valve gaskets, each containing at least one positioning protrusion and at least one positioning slot which interact with each other to orient the two valve gaskets to a particular position relative to each other.

These and other objects can be obtained by the disclosed hemostasis valve and hemostasis cannula unit which are disclosed by the present disclosure.

SUMMARY OF THE INVENTION

This invention involves a hemostasis cannula unit, which includes a longitudinally extended housing having a first and second opposing end, a cap enclosing the first end containing an opening to permit insertion of a dilator or catheter into the longitudinally extended housing, and a hemostasis valve, which consists of a pair of identical valve gaskets compressed together by the valve housing.

The invention also involves a hemostasis valve comprised of two separate, identical, valve gaskets, wherein the proximal valve gasket is maintained in a fixed position relative to the distal valve gasket by the use of at least one cooperating positioning protrusion and slot present in each valve gasket.

The invention also involves a hemostasis valve comprised of two separate, but identical valve gaskets, wherein the center of each valve gasket is very thin in comparison to the overall thickness of the valve gasket.

The invention also involves a hemostasis valve comprised of two separate but identical valve gaskets, each containing a slit, wherein each of the slits is angled at an angle of about 30 to about 85 degrees from the surface of the face of the valve gasket.

The invention also involves a hemostasis valve comprised of two separate, but identical valve gaskets, each of which contains a conical receiving area and each of which contains a centering or guiding hole.

The invention also involves a hemostasis valve comprised of two separate, but identical valve gaskets, wherein the entry face of the proximal valve gasket and the exit face of the distal valve gasket each contains concentric rings extending from the respective surfaces of the two valve gaskets, wherein these concentric rings are placed under compression when the hemostasis valve is placed within a hemostasis valve housing.

The invention also involves a hemostasis valve comprised of two separate, but identical valve gaskets, wherein the sides of each of the hemostasis valve gaskets contains—a beveled edge which extends toward the inside wall of the valve housing when a medical device is inserted through the hemostasis valve.

The invention also involves a hemostasis valve comprised of two separate, but identical valve gaskets, wherein the distal face of the proximal gasket and the proximal face of the distal gasket maintain contact with each other when a medical device is inserted through the hemostasis valve.

The invention also involves a hemostasis valve comprised of two separate valve gaskets, each of which contains an angled slit wherein the angled slit in the proximal gasket cooperates with a proximal surface of the distal gasket and the angled slit in the distal gasket cooperates with the distal surface of the proximal gasket to effect sealing of the valve upon removal of a medical instrument therefrom.

BRIEF DESCRIPTION OF THE DRAWINGS

FIG. 5 is a distal, perspective view of the proximal valve gasket of the hemostasis valve.

FIG. 5A is a side view of the proximal valve gasket of FIG. 5 with an acutely angled slit.

FIG. 5B is a side view of the proximal valve gasket of FIG. 5 with a perpendicularly angled slit.

FIG. 6 is a distal end view of the distal valve gasket of the hemostasis valve with an acutely angled slit.

FIG. 6B is a side, cut away view of the distal valve gasket of FIG. 6 showing the thickness (60) of the slit, the thickness (62) of the slit and the guiding hole and the thickness (64) of the valve gasket between its entry and exit faces.

FIG. 7 is a proximal end view of the distal valve gasket of FIG. 6.

FIG. 8 is a cut away distal plan view of the hemostasis valve with a medical device, in section, inserted therethrough.

DETAILED DESCRIPTION OF INVENTION

Figure 1:
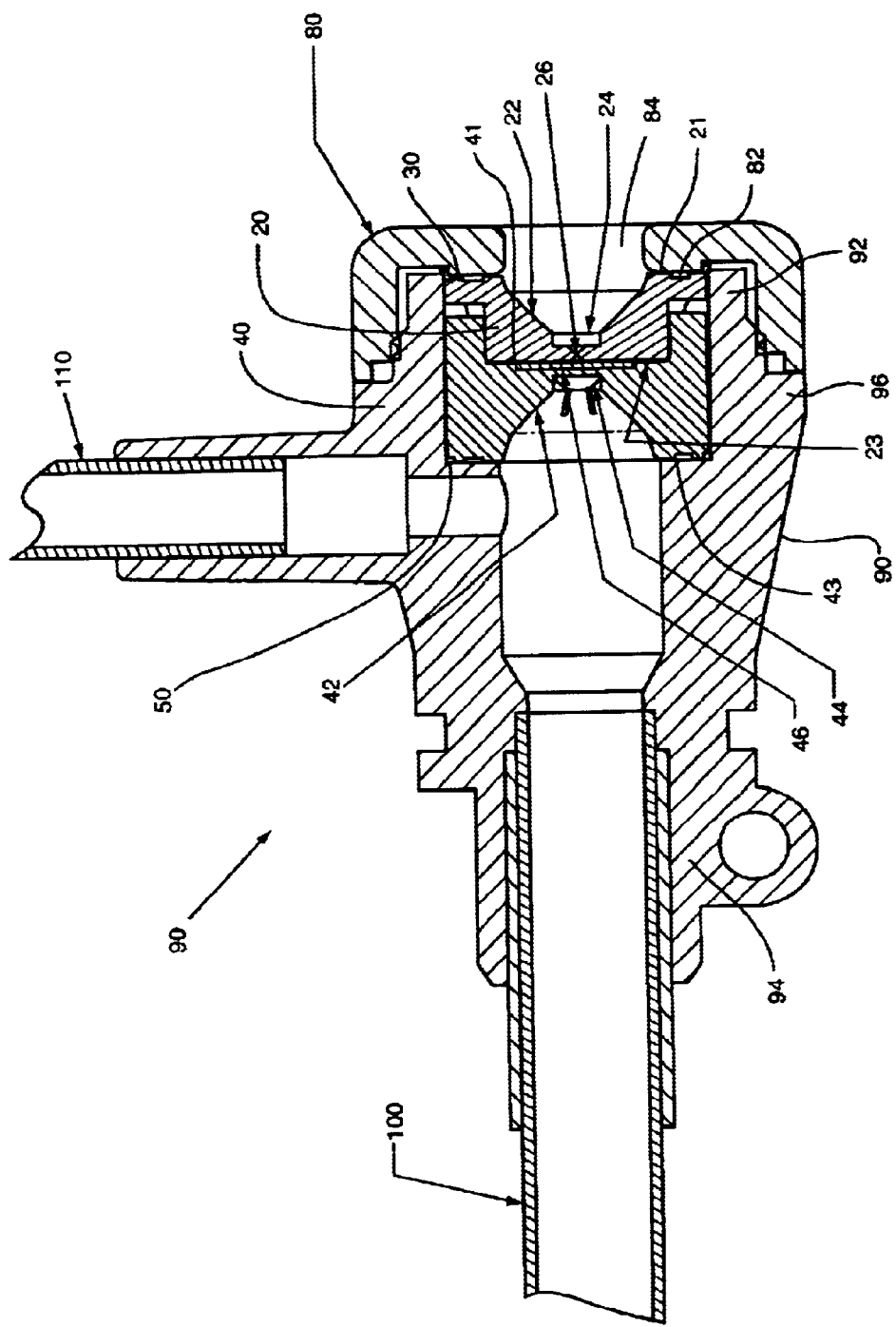
FIG. 1 is a cross-sectional view of the hemostasis valve of the present invention placed within a hemostasis cannula assembly.
Figure 2:
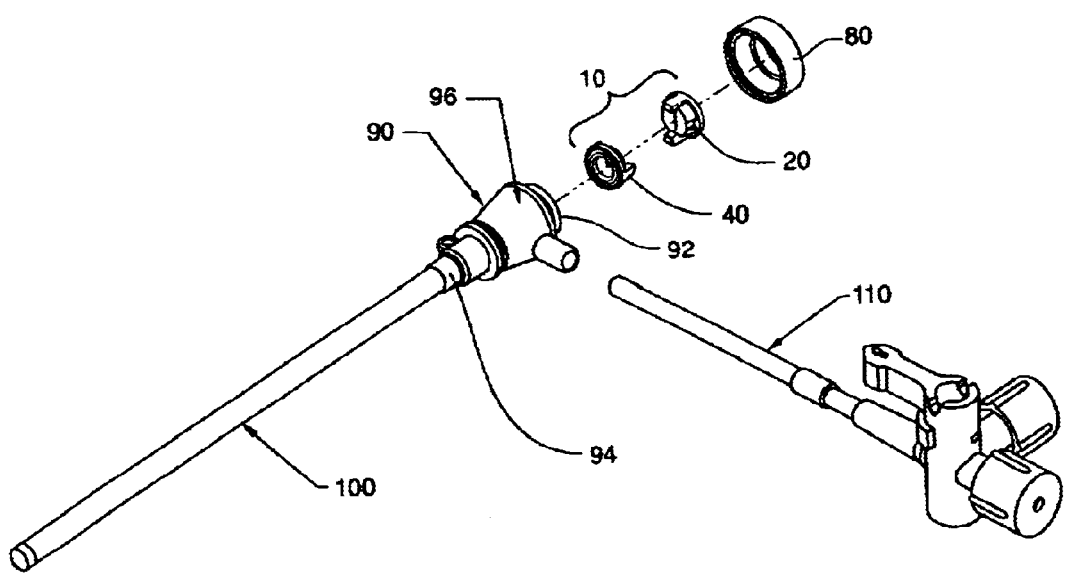
FIG. 2 is an exploded view of the hemostasis cannula assembly of FIG. 1 showing the components thereof, including the proximal and distal valve gaskets of the hemostasis valve.

The high performance hemostasis valve (10) of the present invention is preferably incorporated in a hemostasis cannula assembly (70) as shown in FIGS. 1 and 2, which is used, for example, for various cardiac catheterization procedures in which a dilation catheter or treating catheter advances over a small guidewire into a blood vessel.

The hemostasis cannula assembly (70) is formed of five major components, as shown in FIGS. 1 and 2. The first of these components is the cap (80), which is attached to the proximal end of the second component—the longitudinally extended valve housing or hub (90). The valve housing (90) has proximal and distal opposing openings through which elongated cylindrical medical devices are inserted into and out of the interior of the valve housing or hub (90). The cap (80) and valve housing (90) of the cannula assembly (70) are preferably made from a relatively rigid thermoplastic material, such as a high-density polyethylene or an acrylonitrile-butadiene-styrene copolymer. The cap (80) may be secured to the body (96) of the valve housing (90) by mechanical means using threads, snap fittings, etc. or by gluing, but preferably it is secured by ultrasonic welding or heat adhesion.

Figure 3:
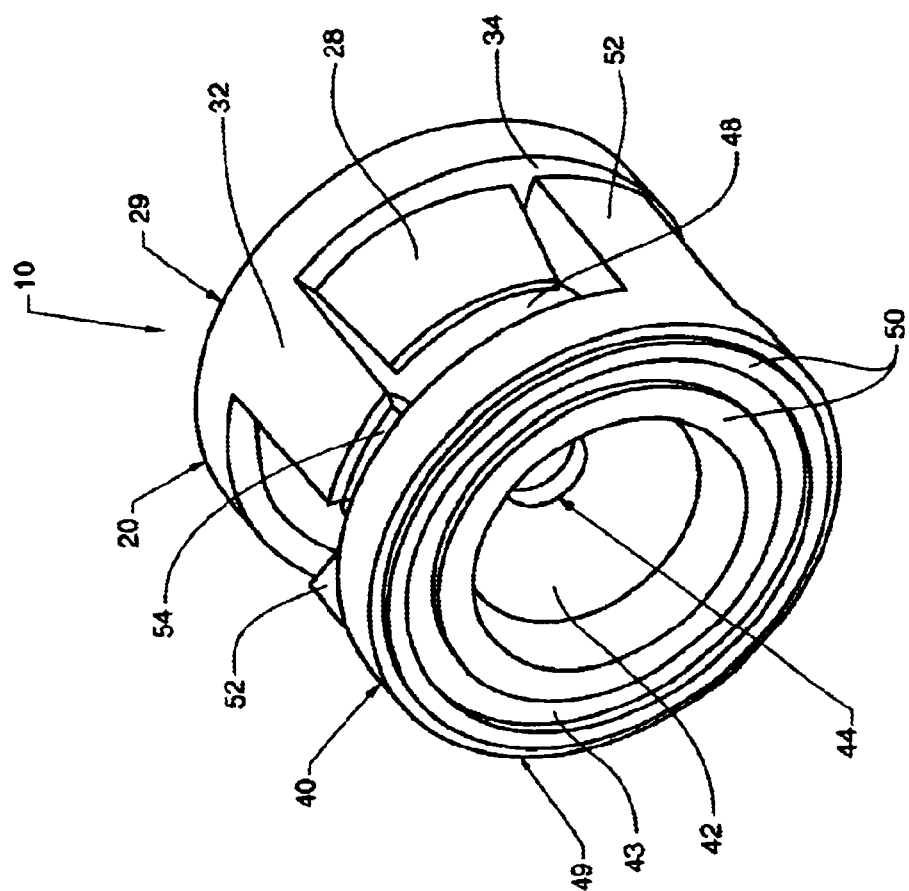
FIG. 3 is a distal, perspective-view of the hemostasis valve showing the proximal and distal valve gaskets joined together.

The third and fourth major components of the hemostasis cannula assembly (70) of the present invention form the hemostasis valve (10) and consist of a proximal valve gasket (20) and a distal valve gasket (40) as shown in FIGS. 1, 2 and 3. An entry face (21) of the proximal valve gasket (20) contacts the inner surface of the cap (80) of the hemostasis cannula assembly (70) and an exit face (23) of the proximal valve gasket (20) contacts an entry face (41) of the distal valve gasket (40), as shown in FIG. 1. An exit face (43) of the distal valve gasket contacts a surface on the interior of the valve housing (90) as shown in FIG. 1 to hold the valve gasket (10) securely within the valve housing (90). The valve gaskets (20, 40) are made from a pliant, high elastic polymeric material, such as a silicone rubber, or a thermoplastic elastomer (olefinic, styrenic, polyamide-based, polyester-based, or a hydrocarbon rubber, such as polybutadiene, polyisoprene, or natural rubber), which can readily and repeatedly permit passage of elongated cylindrical medical devices (120) of varying diameters through the hemostasis valve (10).

The final major component of the hemostasis cannula assembly (70) of the present invention is the tubular introducer sheath (100) as shown in FIGS. 1 and 2, which is preferably made of a biocompatible thermoplastic material, such as a high density polyethylene (HDPE), polypropylene, fluoropolymer, polyether block amide (PEBA), polyamide (PA), polyvinyl chloride (PVC), polyurethane-based thermoplastic elastomer or a blend of the aforementioned polymeric materials. A multilayered tubular structure may also be used to co-extrude the introducer sheath (100) using different combinations of the aforementioned polymeric materials. The sheath (100) is inserted within the distal end (94) of the valve housing or hub (90) and is secured in place preferably by heat adhesion or ultrasonic welding to provide an exit from the interior of the valve housing (90).

A side port (110) is preferably secured to or formed into the valve housing (90) distal to the hemostasis valve (10), as shown in FIGS. 1 and 2, to provide for the perfusion and aspiration of fluids through the sheath (100).

The introducer sheath (100) maintains the percutaneous opening, or access site to the vasculature, initially made with other devices, such as a hypodermic needle or scalpel, and provides an entrance point for a dilator or obturator, as well as catheters and guidewires. The introduction of the introducer sheath (100) into the blood vessel is accomplished by a dilator advancing over the guidewire, both of which are advantageously passed through the introducer sheath (100) and valve (10). Once the introducer sheath (100) is advanced a sufficient distance within the chosen blood vessel, the guidewire and dilator are removed in favor of insertion of the therapeutic catheter system, as shown, for example, in FIG. 10.

The proximal valve gasket (20) and the distal valve gasket (40) form the hemostasis valve (10) as shown in FIGS. 1, 2 and 3. The proximal valve gasket (20) and the distal valve gasket (40) are assembled by aligning and inserting one or more, preferably two, positioning protrusions (32, 52) located on each of the valve gaskets (20, 40) within one or more, preferably two, positioning slots (34, 54) located on each of the valve gaskets (20, 40) as shown in FIG. 3. The hemostasis valve (10) is inserted into the valve housing (90) at its proximal end (92), as shown in FIG. 1. The cap (80) is then secured onto the proximal end (92) of the valve housing (90). Upon assembly, a guiding cone or conical receiving area (22) of the proximal valve gasket (20) is approximately in alignment with an opening (84) through the cap (80). An inner circular section (82) of the cap (80), which extends outward from the inner surface of the cap, preferably imposes a slight axial compression of the proximal valve gasket (20) against the distal valve gasket (40) after assembly of the hemostasis cannula assembly (70). As will be discussed in more detail later, the entry face (21) of the proximal valve gasket (20) and the exit face (43) of the distal valve gasket each contain elevated concentric rings (30, 50) as shown, for example, in FIGS. 1, 3, 4 and 6, which are compressed when the hemostasis valve (10) is inserted within the valve housing (90) and secured in place when the cap (80) is secured to the proximal end of the valve housing (90). Preferably the pressure against the hemostasis valve (10) compresses it at least about 2 percent and preferably from about 2 to 5 percent within the valve housing (90).

The proximal valve gasket (20) and the distal valve gasket (40) are preferably formed with an identical shape and structure. Having the same structure obviously reduces the overall cost of manufacture of the hemostasis valve (10). Further, there are many advantages to this structure which are discussed in more detail later. However, for purposes of this discussion, the description of the structure and shape of the proximal valve gasket (20) applies equally to the structure of the distal valve gasket (40).

Figure 4:
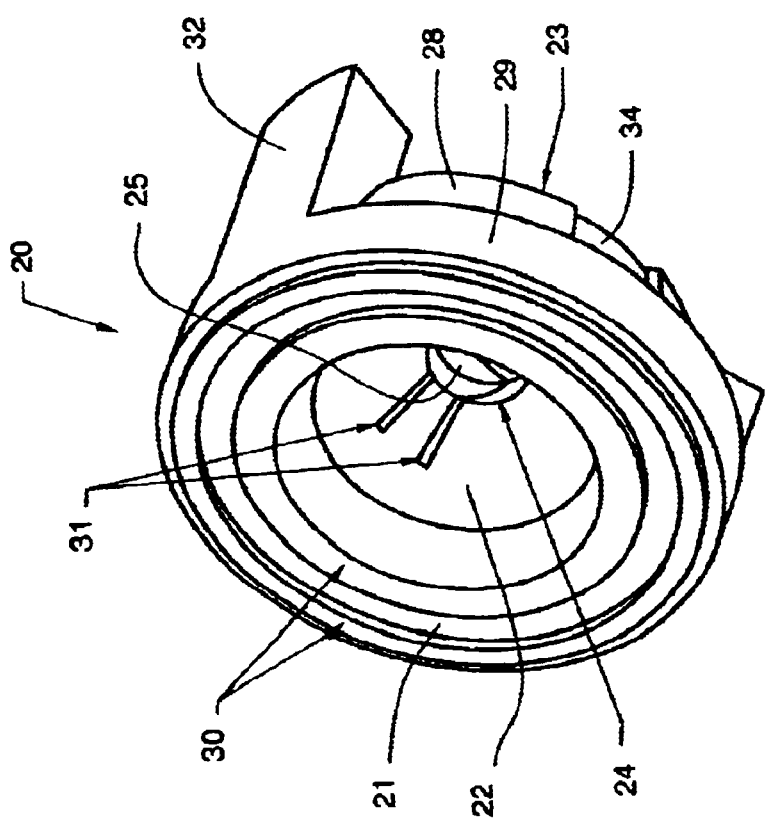
FIG. 4 is a proximal perspective view of the proximal valve gasket with an acutely angled slit.

The proximal valve gasket (20) contains a conical receiving area or guiding cone (22) which tapers into a centering or guiding hole (24), as shown in FIGS. 1, 4, 5A and 5B. The conical receiving area or guiding cone (22) tapers at an angle from about 20 to about 80 degrees, and preferably from about 20 to about 60 degrees from the entry face (21) of the valve gasket (20). The centering hole (24) acts as a sealing neck when a catheter of larger diameter passes through the hemostasis valve (10). The centering hole (24) can be formed in any cross section, consisting with the outer geometry of the medical instruments inserted therein. For example, the cross section of this hole (24) could be rectangular, triangular, elliptical or round. If a circular cross section is utilized for the centering hole (24) as shown in FIGS. 4 and 5A, it is preferred that its diameter be that of the smallest dilator that is utilized with the hemostasis cannula assembly (70). A circular cross section is preferred, as shown in FIGS. 4 and 5A, such as that which would accommodate a 4 French (1.33 mm) dilator. The guiding hole (24) terminates distally in a flat surface (25).

Taken together the guiding or centering hole (24) (FIGS. 4 and 5A) and the conical receiving area (22) guide elongated medical devices to the center of the proximal valve gasket (20) of the hemostasis valve (10) to permit easy insertion of a wide variety of catheters with different diameters into, and through, the hemostasis valve (10) while still providing excellent "feel" for clinicians.

Extending distally from the guiding hole (24) of the valve gasket (20) is the slit (26) of the valve gasket (20), which entirely passes through the remaining portion of the valve gasket (20), to its exit face (23) as shown in FIGS. 1 and 5A. This slit (26) is preferably a single slit with its proximal end located at or near the center of the guiding hole (24). The width of the slit (26) is from about 0.070 in. (1.8 mm) to about 0.15 in. (3.8 mm), and preferably from about 0.09 in. (2.3 mm) to about 0.12 in. (3.0 mm).

Figure 9:
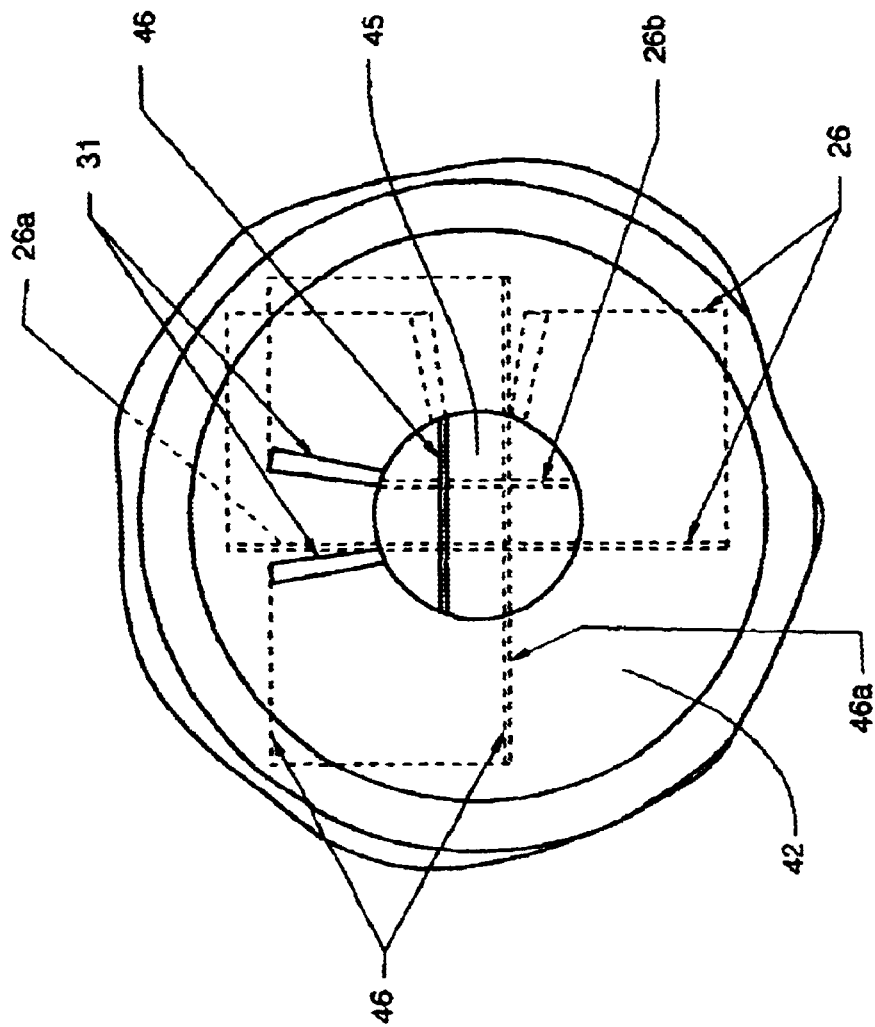
FIG. 9 is a partially cut away enlarged distal plan view of the hemostasis valve of FIG. 3 showing the cuts of the angled slits extending through the respective gaskets.

As shown in FIG. 4, slit (26) is preferably cut at an angle from about 5 to about 70 degrees away from being perpendicular to the outer surface (23) of the proximal valve gasket (20). Optimally the angle of this cut is from 44–46 degrees out of perpendicular. The slit (26) is preferably axially centered so that its proximal edge and distal edge are equidistant from the long central axis of the hemostasis cannula assembly (70). Slit (26) is also centered radially. These locational principals are also illustrated by reference to the slits (26, 46) as shown in FIG. 9. Because the width of slit (26) (and, correspondingly slit (46)) is preferably greater than the inner diameter of guiding hole (24), the slit extends partially over and partially under conical area (22), leaving two sections (31) of slit (26) visible as shown on FIG. 4. (See the corresponding cut sections (51) of the distal valve gasket (40) as shown on FIG. 6.) Angling slits (26, 46) in the manner described creates thin regions of elastomeric material at the leading and trailing portions of the slits (26, 46) and, thus makes those areas more responsive to the surface geometry of the medical device (120), which may be placed therein. Because the thin areas of the elastomer conform to said surface geometry, the ingress of air and other vascular contaminants is also better prevented. Likewise, egress of blood between the medical device and inner regions of the valve (10) is precluded. Other advantages are hereinafter apparent. Alternatively, as shown in FIG. 5B, the slit (26) may extend at a perpendicular angle to the surface of the exit face (23) and to the surface (25) of the guiding hole (24).

The exit face (23) of the proximal valve gasket (20), includes a depressed, beveled edge (28), as shown in FIGS. 5, 5A and 5B, which is angled at an angle from about 20 to about 90 degrees and preferably from about 30 to about 60 degrees from the exit face (23) of the proximal valve gasket (20). By angling the beveled edges (28) of the proximal valve gasket (20) in the manner shown in FIGS. 5, 5A and 5B, when an elongated cylindrical medical device is extended through the hemostasis valve (10), the blood pressure acting on the hemostasis valve (10) generally is converted from an axial pressure to a radial pressure producing a seamless pair of valve gaskets (20, 40), thereby producing a better "feel" for the clinician. In addition, the material of this beveled edge (28) of the proximal valve gasket (20) expands radially when the indwelling medical device is inserted through the hemostasis valve (10). The space between the beveled edge (28) of the proximal valve gasket (20) and the inner surface of the valve housing (90) is gradually filled with the expanded material of the proximal valve gasket (20), thereby reducing the difficulty of introducing the medical device through the hemostasis valve (10).

The second major component of the hemostasis valve (10) is the distal valve gasket (40), as shown in FIGS. 6, 6B and 7. It is designed to complement the proximal valve gasket (20) and operate in coordination therewith to provide improved sealing for small guidewires. It is designed with the same shape as that of the proximal valve gasket (20), only reversed, as shown in FIG. 3, such that the entry face (41) of the distal valve gasket (40) cooperates with the exit face (23) of the proximal valve gasket (20), as shown in FIG. 1. Gaskets (20) and (40) being preferably the same shape has advantages that will be readily apparent. For example, one mold can produce parts that can serve as either gasket. Similarly, the same processes can be used to stock and handle inventory parts.

The distal valve gasket (40) also includes a beveled edge (48). This beveled edge (48) of the distal valve gasket (40) works in coordination with the beveled edge (28) of the proximal valve gasket (20). It is angled with a complementary angle to the angle of the beveled edge (28) of the proximal valve gasket (20).

Near the center of the distal valve gasket (40) is its slit (46), as shown in FIGS. 6, 6B, 7 and 9, which is preferably placed in a position perpendicular to the position of the slit (26) of the proximal valve gasket (20) when the proximal valve gasket (20) and the distal valve gasket (40) are joined together as shown in FIGS. 1 and 3. The width of the slit (46) of the distal valve gasket (40) is preferably the same width as is the width of the slit (26) of the proximal valve gasket (20). The slit (46) of the distal valve gasket (40) extends through the distal valve gasket (40) to a guiding, centering or guard hole (44) as shown in FIGS. 6 and 6B. The guiding hole (44) of the distal valve gasket (40) performs an important function by assisting in the guiding of indwelling medical devices through the hemostasis valve (10), especially curved medical devices. When those curved medical devices pass through the centering hole (24) and slit (26) of the proximal valve gasket (20), the curved medical device may tend to stray from the center of the hemostasis valve (10). By having a second centering or guiding hole (44) present in the distal valve gasket (40), the curved medical device passing through the hemostasis valve (10), is encouraged to pass straight through the hemostasis valve (10). Guiding hole (44) originates proximally at flat surface (45).

In order to reduce the resistance of the hemostasis valve (10) to the passage of medical devices therethrough, it is preferable that the distance that the medical valve must pass through the hemostasis valve (10) be kept to a minimum. This is accomplished using the hemostasis valve (10) of the present invention by the "back-to-back" arrangement of the proximal valve gasket (20) against the distal valve gasket (40). By this "back-to-back" arrangement, the thickness of the hemostasis valve (10) where the medical device passes through the hemostasis valve (10) is kept at a minimum. In one preferred embodiment the thickness of this portion of the hemostasis valve (10) in relation to the overall thickness of the hemostasis valve (10) is kept to a minimum. For example, in FIGS. 5B and 7B, the thickness of the slit area (between exit face (23) and flat surface (25) and entry face (41) and flat surface (45), respectively) of both the proximal and distal valve gaskets (20, 40) are preferably from about 0.010 inches (0.25 mm) to about 0.03 inches (0.8 mm). This is designated at FIG. 6B, reference number 60. The thickness of this slit (46) is designated by number 60 on FIG. 7. The longitudinal thickness of the centering hole (44) is approximately the same thickness as is the thickness of the slit (46). Thus, the overall longitudinal thickness of the slit area (60) and centering hole (44) in combination, which is designated by numeral (62), is preferably from about 0.02 inches (0.5 mm) to 0.06 inches (1.6 mm).

In contrast, the thickness of the proximal valve gasket (20) or the distal valve gasket (40) from their respective entry faces (21, 41) to their respective exit face (23, 43) is considerably thicker than the thickness of the respective slits (26, 46) designated by number 64, or the thickness of the respective slit area (60) and centering holes (24, 44) combined (62). In determining the thickness, for example, of the distal valve gasket (40) (or the proximal valve gasket (20) the thickness is measured from its entry face (41) on the proximal side of the distal valve gasket (40) to its exit face (43) on the distal side of the distal valve gasket (40). This thickness, designated by number (64), of the distal valve gasket (40) is preferably from about 0.07 inches (1.8 mm) to about 0.15 inches (3.8 mm). Thus, preferably, the thickness (60) of the slit (46) of the distal valve gasket (40) is less than about 25 percent of the overall thickness (64) of the distal valve gasket and more preferably from about 10 to about 40 percent of that thickness (64).

The split slits (26, 46) formed by the slit (26) of the proximal valve gasket (20) and the slit (46) of the distal valve gasket (40) act as the primary crisscross sealing barrier to prevent the flow of blood and air through the hemostasis valve (10). In order to assure the proper alignment of the proximal valve gasket (20) and its slit (26) with the slit (46) of the distal valve gasket (40), one or more, preferably two, positioning protrusions (32) are provided in the outer edge (29) of the proximal valve gasket (20) which align with one or more, preferably two, positioning slots (54) present in the outer edge (49) of the distal valve gasket (40), as shown in FIG. 3. By aligning the respective positioning protrusion(s) (32) of the proximal valve gasket (20) with the positioning slot(s) (54) of the distal valve gasket (40), the respective slits (26, 46) align radially, perpendicularly to each other to assure proper relative position of the distal valve gasket (40) and the proximal valve gasket (20) and to form the preferred crisscross sealing pattern within the hemostasis valve (10), as shown in FIGS. 1 and 3. In addition, in a preferred embodiment the slit (46) of the distal valve gasket (40) is located at a position between the respective positioning protrusions (52), as shown on FIG. 7, and is perpendicular to a line formed between the respective positioning slots (54). The proximal valve gasket (20) contains a similar structure for its slit (26) as shown in FIG. 5. Preferably, there is an additional pair of positioning protrusions (52) provided in the outer edge (49) of the distal valve gasket (40) which align with one or more, preferably two, positioning slots (34) present in the outer edge (29) of the proximal valve gasket (20) as shown in FIG. 3. (Although the gaskets (20, 40) are preferably aligned so that the respective slits (26, 46) align perpendicular to each other the slits (26, 46) may be aligned so that the angle between the slits (26, 46) is as much as 45 degrees out of perpendicular, or more, if desired.)

This structure of complimentary positioning protrusions (32, 52) and positioning slots (34, 54) in each of the proximal and distal valve gaskets (20, 40) results in the proper alignment of the proximal valve gasket (20) in relation to the distal valve gasket (40) when the two gaskets are joined together. In addition, in a preferred embodiment the distance between the inner surface of each pair of positioning protrusions (52), as shown in FIG. 7, is slightly less than the inner diameter of the slots (54) provided in the distal valve gasket (40). With this structure, when the respective positioning protrusions (32) of the proximal valve gasket (20) are forced within the slots (54) of the distal valve gasket (40), there is an outward pressure placed on the respective positioning protrusions (32). This outward pressure slightly stretches the slit (26) of the valve gasket (20) as it is pulled toward the respective protrusions (32). This makes for a better seal to prevent the flow of blood through the valve (10) and forces the slit (26) tightly closed even when no indwelling medical device is present within the hemostasis valve (10).

When using the angled slit as shown in FIGS. 5A and 6, the trailing or distal edge of slit (26) exits valve gasket (20) at exit face (23). Because slit (46) is perpendicular to slit (26), they intersect at a single point. When gasket (20) and gasket (40) are in operative engagement, the distal edge of slit (26) is urged closed by entry face (41). Thus, the thinner distal elastomeric region of slit (26) retains its ability to conform to the outer diameter of an indwelling medical device (120), but shares the added benefit of being urged closed by less elastomeric, thicker entry face (41). Similarly, the leading or proximal edge of slit (46) enters valve gasket (40) at exit face (23). Thus, exit face (23) supports the thinner proximal elastomeric region of slit (46) which, again, retains its ability to conform to the outer diameter of an indwelling medical device. The axial distal edge of slit (46) also has a thin region. This region is thin and pliant to follow the contour of the medical device, but it is urged closed by pressure exerted from a fluid (blood) column in communication with the normally pressurized circulatory system.

The three thin elastomeric regions of slits (26 and 46) are not only more responsive to the medical device contours, they more quickly relax from a state of deflection, sometimes constantly for a period of many hours, to completely isolate the blood from the operating room environment. In other words, the thin regions allow the valve (10) to close completely and quickly because they relax to the closed state faster than thicker regions that have been deformed for lengthy periods of time.

The entry face (21) of the proximal valve gasket (20) preferably has the same structure and shape as the exit face (43) of the distal valve gasket (40). In a preferred embodiment, each of these faces (21, 43) contains one or more concentric rings (30, 50) raised above the surface of the faces (21, 43). For example, on FIGS. 3, 4 and 6 note the two concentric rings (30, 50) on the exit faces (23, 43) of the valve gaskets (20 40). These concentric rings (30, 50) are raised slightly above the surface of the exit face (43). Each of these concentric rings (30, 50) are put under pressure when the cap (80) is secured onto the valve housing (90) as shown in FIG. 1. Because there is a lesser amount of elastomic material being put under pressure because the concentric rings (30, 50) are raised, a better circumferential seal is formed within the valve housing (90) by the hemostasis valve (10) against blood flow around the outside of the hemostasis valve (10) when no elongated medical device is present within the hemostasis valve (10).

FIG. 8 shows a deformed configuration for the respective slits (26, 46) when an elongated cylindrical member (120) passes through the hemostasis valve (10). To form this configuration, two curvilinear triangle-like interstices (27, 47) are formed at the ends of the respective slits (26, 46). The interstices (27) of the proximal valve gasket (20) and those (47) of the distal valve gasket (40) interweave when a cylindrical member (120) passes through the distal valve gasket (40) and proximal valve gasket (20) as shown in FIG. 8. The interweaving of the interstices (27, 47) from the respective proximal valve gasket (20) and distal valve gasket (40) creates a mutual barrier against the leakage of blood through the hemostasis valve (10). Leakage of blood occurs only if the two neighboring, interweaving interstices (27, 47) are connected. If the diameter of the elongated cylindrical member (120) inserted is too small, the two neighboring interstices (27, 47) may remain connected, dependent on the degree of the radial compression of the hemostasis valve (10). In such cases, leakage of blood is prevented by the initial radial compression. If the diameter of the elongated cylindrical member (120) is too large, it is possible for interweaving interstices of a conventional hemostasis valve to connect, forming a passage for the leakage of blood around the circumference of the catheter. This becomes a more serious problem when the inserted medical device (120) is circumferentially turned by the clinician during the insertion. However, due to the shape and structure of the proximal valve gasket (20) and distal valve gasket (40) respectively, leakage of blood can be limited or prevented by the complimentary sealing capacity of the guiding holes (24, 44), the diameter of which is smaller than the diameters of some large sized catheters used with the present hemostasis valve (10).

FIG. 9 depicts an enlarged distal view of the axial portion of hemostasis valve (10). The axial distal edge of slit (46) can be seen in plan view upon flat surface (45) with its proximal and distal regions depicted in phantom. The proximal edge of slit (46) is depicted in phantom and designated at reference numeral 46a. Similarly the distal edge of slit (26) (upon exit face (23), FIG. 5B) is depicted in phantom and designated at reference numeral 26a. The proximal and axial portion of slit (26) (upon flat surface (25), FIGS. 4 and 5A) is depicted in phantom and designated at reference numeral 26b.

Figure 10:
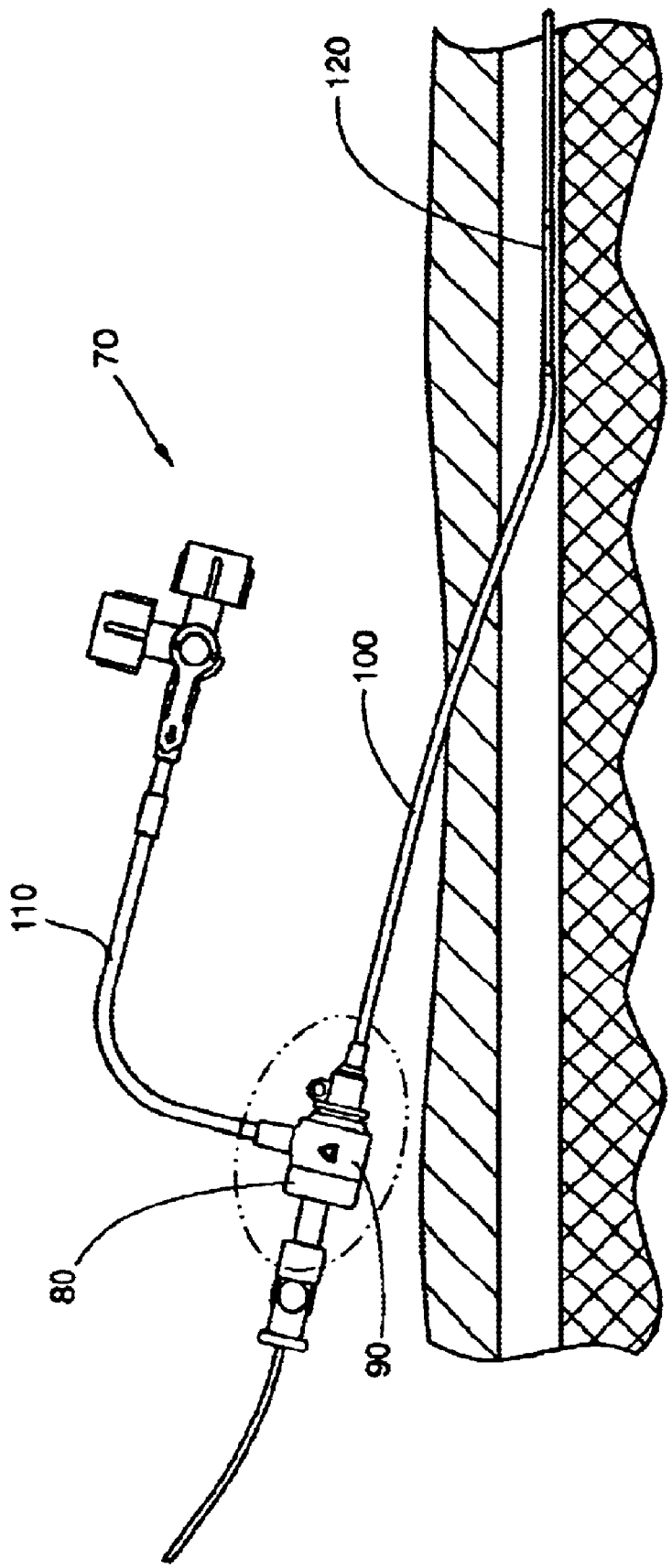
FIG. 10 is a side, partially cut-away view of the hemostasis cannula assembly of FIG. 1 with a medical device inserted through the assembly.

When an elongated medical device (120) passes through the hemostasis valve (10) of the present invention as shown in FIG. 10, the deformation of the valve (10) structurally self-adjusts in a radial direction from the axial direction due to the axial rigidity of the proximal and distal valve gaskets (20, 40). In addition, the overall thinness of the slits (26, 46) of the proximal valve gasket (20) and distal valve gasket (40) respectively, reduces the resistance to the passage of medical devices (120) through the valve gasket (10). Also, during insertion the beveled edges (28, 38) of the proximal valve gasket (20) and the distal valve gasket (40) extends toward the wall of the valve housing (90). However, because this radial stretching is perpendicular to the slit (26) in the valve gasket (20), it does not affect the sealability of the hemostasis valve (10).

The slits (26, 46) are also stretched by the structure of the respective positioning protrusions (32, 52) in relation to the respective positioning slots (34, 54). This also means that the overall insertion resistance, which previously came from the friction of the medical device (120) passing through the slits (26, 46), of the hemostasis valve (10), is reduced.

The back pressure of blood acts against the exit face (43) of the distal valve gasket (40). Due to the structural features of the present hemostasis valve (10), including specifically its relative thinness where medical devices pass through, the proximal valve gasket (20) and the distal valve gasket (40) are maintained substantially in contact during the insertion of elongated medical devices, forming a seamless sealing pair with reduced insertion resistance.

When retracting a catheter during the catheterization procedure, the axially rigid structural features of the hemostasis valve (10) also self-adjust the deformation of the valve (10) primarily in a radial direction. The back pressure, along with the retracting resistance force formed by pressing the proximal valve gasket (20) tightly in contact with the distal valve gasket (40), also self-cleans the elongated cylindrical medical device (120) while it is being retracted.

Due to these structural features of the hemostasis valve (10) and the difference in the thinness of the proximal valve gasket (20) and the distal valve gasket (40) at the specific location where the medical device (120) passes through, the deformations of the proximal valve gasket (20) and distal valve gasket (40) are primarily in a radial direction instead of an axial direction during both insertion and retraction of the elongated cylindrical medical device. Also, because the hemostasis valve (10) occupies approximately the same amount of space in the valve housing (90) prior to, during, and after the insertion and retraction of the elongated cylindrical medical device, seepage of air into the blood stream is prevented. With the hemostasis cannula assembly (70) in place, it is possible to insert medical devices having a wide range of diameters with ease.

In use, the elongated cylindrical medical device (120) is inserted through the circular opening (84) in the cap (80) and into the hemostasis valve (10). If the medical device (120) is inserted slightly off center it will be guided by the conical receiving area or guiding cone (22) to the guiding hole (24) of the proximal valve gasket (20). The medical device (120) is then advanced into the slit (26) of the proximal valve gasket (20), into the slit (46) and out of the guiding hole (44) of the distal valve gasket (40). After exiting from the hemostasis valve (10), the medical device (120) is advanced through the introducer sheath (100) and into the blood vessel. Any blood which flows between the sheath (100) and the medical device (120) up into the interior of the valve housing (90) is prevented from escaping to the exterior due to the sealing action of the pair of slits (26, 46) and proximal valve gasket (20) and distal valve gasket (40) of—the hemostasis valve (10) around the body of the medical device (120). Due to the unique structural features of the hemostasis valve (10) of the invention and the structural relationships between the proximal valve gasket (20) and the distal valve gasket (40), resistance to insertion is reduced, and self-cleaning of blood off the medical device is provided with no seepage of air into the blood stream during retraction.

As many widely different embodiments of the present invention of the hemostasis valve (10) can be made without departing from the spirit, or essential characteristics, and the scope thereof, it is understood that this embodiment of the present invention is merely an illustration of the invention, and provides no limitation on its scope. Changes may be made to the specific embodiment of invention without departing from the overall invention.

We claim:

1. A hemostasis valve comprising
a proximal valve gasket comprising a generally flattened disk containing a slit and a positioning slot, and
a distal valve gasket comprising a generally flattened disk containing a slit and a positioning protrusion, wherein said positioning protrusion extends axially away from a face of the generally flattened disk toward a face of the proximal valve, gasket, and wherein the positioning protrusion of the distal valve gasket extends within the positioning slot of the proximal valve gasket and wherein when the positioning protrusion is placed within the positioning slot, axially rotation of the proximal valve gasket in relation to the distal valve gasket is substantially prevented.

2. The hemostasis valve of claim 1 wherein the distal valve gasket further comprises a raised circular ring on a distal face of the generally flattened disk.

3. The hemostasis valve of claim 1 wherein the proximal valve gasket and the distal valve gasket are formed in the same shape.

4. The hemostasis valve of claim 1 wherein the proximal valve gasket further comprises a second positioning slot, wherein the distal valve gasket further comprises a second positioning protrusion and wherein the inner diameter of the positioning protrusions is less than the diameter of the positioning slots.

5. The hemostasis valve of claim 4 wherein the pair of positioning protrusions are approximately 180 degrees apart from each other on an outside edge of the distal valve gasket.

6. The hemostasis valve of claim 5 wherein the slit of the distal valve gasket runs between the two positioning protrusions.

7. The hemostasis valve of claim 1, wherein the proximal valve gasket further comprises a conical receiving area and a guiding hole in communication with the slit, and wherein the distal valve gasket further comprises a conical receiving area and a guiding hole in communication with the slit of the distal valve gasket.

8. The hemostasis valve of claim 1 wherein the slit of the proximal valve gasket is angled from about 5 to about 70 degrees away from a perpendicular line extending away from a flattened surface of the flattened disk.

9. A hemostasis cannula unit comprising
a longitudinally extended valve housing having a first opening and a central longitudinal chamber communicating with a second opening;
a cap secured to the valve housing enclosing the first opening of the valve housing and providing an opening to permit insertion of a medical device into the first opening of the housing through the central chamber and out the second opening; and
a hemostasis valve contained within the valve housing comprising a proximal valve gasket comprising a generally flattened disk containing a slit and a positioning slot and a distal valve gasket comprising a generally flattened disk containing a slit and a positioning protrusion, wherein said positioning protrusion extends axially away from a face of the generally flattened disk toward a face of the proximal valve gasket, and wherein the positioning protrusion of the distal valve gasket interacts with the positioning slot of the proximal valve gasket and wherein when the positioning protrusion is placed within the positioning slot, axial rotation of the proximal valve gasket in relation to the distal valve gasket is substantially prevented.

10. The hemostasis cannula unit of claim 9 wherein the proximal valve gasket further comprises a beveled portion and wherein the beveled portion forms a space between the hemostasis valve and an inner surface of the valve housing when the hemostasis valve is present within the valve housing.

11. The hemostasis cannula unit of claim 2 wherein the cap when secured to the valve housing places the hemostasis valve under compression such that the thickness of the hemostasis valve is compressed by at least about 2 percent.

12. The hemostasis cannula unit of claim 9, wherein upon introduction of a medical device through the hemostasis valve, a distal face of the proximal valve gasket and a proximal face of the distal valve gasket maintain in contact when the medical devise is inserted through the hemostasis valve.

13. A process for introduction of a medical device into a vasculature of a patient comprising,
    introducing the hemostasis cannula unit of claim 2 into the vasculature of a patient and,
    introducing a medical device through the hemostasis valve of the hemostasis cannula unit into the vasculature of a patient.

14. A hemostasis valve comprising
    a proximal valve gasket comprising a generally flattened disk containing an entry and exit face, a slit extending through that disk, a guiding hole and a positioning slot, and
    a distal valve gasket comprising a generally flattened disk having an entry face and an exit face, a slit extending through that disk, a guiding hole and a positioning protrusion, wherein said positioning protrusion extends axially away from said entry face of the generally flattened disk of the distal valve gasket toward the exit face of the proximal valve gasket, and wherein the longitudinal thickness of the area of the proximal valve gasket containing the slit is less than about 40 percent of the overall thickness of the proximal valve gasket between its entry and exit faces.

15. The hemostasis valve of claim 14 wherein the thickness of the area of the distal valve gasket containing the slit is from about 10 percent to about 40 percent of the overall thickness of the distal valve gasket from its entry to its exit face.

16. The hemostasis valve of claim 14 wherein the proximal valve gasket and the distal valve gasket are formed in the same shape.

17. The hemostasis valve of claim 14 wherein the slit of the proximal valve gasket is angled from about 5 to about 70 degrees away from a perpendicular line extending away from the exit face of the flattened disk.

18. A hemostasis valve comprising
    a proximal valve gasket comprising a generally flattened disk containing a slit, a positioning slot and a raised circular ring on a proximal surface of the generally flattened disk, and
    a distal valve gasket comprising a generally flattened disk containing a slit and a positioning protrusion, wherein said positioning protrusion extends axially away from a face of the generally flattened disk toward a face of the proximal valve gasket, and wherein the positioning protrusion interacts with the positioning slot of the proximal valve gasket and wherein when the positioning protrusion is placed within the positioning slot, axial rotation of the proximal valve gasket in relation to the distal valve gasket is substantially prevented.

19. The hemostasis valve of claim 18 wherein the distal valve gasket further comprises a raised circular ring on a distal face of the generally flattened disk.

20. The hemostasis valve of claim 18 wherein the proximal valve gasket and the distal valve gasket are formed in the same shape.

21. The hemostasis valve of claim 18 wherein the slit of the proximal valve gasket is angled from about 5 to about 70 degrees away from a perpendicular line extending away from the exit face of the flattened disk.

22. A hemostasis valve comprising
    a proximal valve gasket comprising a generally flattened disk containing a slit and a positioning slot, and
    a distal valve gasket comprising a generally flattened disk containing a slit and a positioning protrusion, wherein the positioning protrusion of the distal valve gasket interacts with the positioning slot of the proximal valve gasket and wherein when the positioning protrusion is placed within the positioning slot, axially rotation of the proximal valve gasket in relation to the distal valve gasket is restricted, and
    wherein the proximal valve gasket further comprises a second positioning slot, wherein the distal valve gasket further comprises a second positioning protrusion and wherein the inner diameter of the positioning protrusions is less than the diameter of the positioning slots.

23. The hemostasis valve of claim 22 wherein the pair of positioning protrusions are approximately 180 degrees apart from each other on an outside edge of the distal valve gasket.

24. The hemostasis valve of claim 22 wherein the slit of the distal valve gasket runs between the two positioning protrusions.

* * * * *